United States Patent [19]

Poggio et al.

[11] 3,994,945
[45] Nov. 30, 1976

[54] URANIUM ALLYL COMPOUNDS
[75] Inventors: Sergio Poggio, Milan; Gabriele Lugli; Alessandro Mazzei, both of San Donato Milanese, all of Italy
[73] Assignee: Snam Progetti S.p.A., Milan, Italy
[22] Filed: Dec. 4, 1974
[21] Appl. No.: 529,560

Related U.S. Application Data
[63] Continuation of Ser. No. 307,497, Nov. 17, 1972, abandoned.

[30] Foreign Application Priority Data
Nov. 26, 1971 Italy .................................. 31729/71

[52] U.S. Cl. ............................................. 260/429.1
[51] Int. Cl.[2] .......................................... C07F 5/00
[58] Field of Search............ 260/429.1; 252/301.1 R

[56] References Cited
UNITED STATES PATENTS
3,468,921  9/1969  Wilke........................... 260/429.1 X OTHER PUBLICATIONS
Lange, Handbook Of Chemistry, Handbook Pub. Co., Sandusky, Ohio, 1946, pp. 58 and 59.

Primary Examiner—Leland A. Sebastian
Attorney, Agent, or Firm—Ralph M. Watson

[57] ABSTRACT
A new uranium allyl compound, represented by the formula:

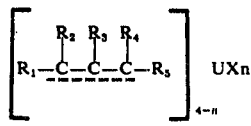

wherein $R_1$, $R_2$, $R_3$, $R_4$, and $R_5$, which may be the same or different, are members of the group consisting of H, alkyl radicals containing from 1 to 10 C atoms, aryl radicals containing from 6 to 10 C atoms, cycloalkyl radicals containing from 4 to 10 C atoms, and alkyl aryl radicals containing from 7 to 10 C atoms, the dotted line linking the three carbon atoms indicates possible delocalization of the valence electrons of the double bond, X is an anion selected from $Cl^-$, $Br^-$ and $I^-$ and $n$ is an integer ranging from 1 to 3. The members of that group of compounds are useful, respectively, as catalysts in the stereospecific polymerization of diolefins and may be prepared by reacting a compound represented by the formula:

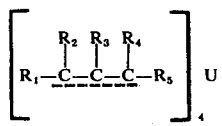

wherein $R_1$, $R_2$, $R_3$, $R_4$ and $R_5$ and the dotted line have the significance given above, with a compound represented by the formulae HX or $X_2$, wherein X has the significance given above.

1 Claim, No Drawings

URANIUM ALLYL COMPOUNDS

This is a continuation of application Ser. No. 307,497, filed Nov. 17, 1972, now abandoned.

The present invention relates to novel uranium allyl compounds and the method for preparing such compounds.

In the preceding patent application No. 16315 A/69 of the Applicant (now Italian Pat. No. 869,752) there were described the preparation of uranium tetraallyl derivatives having the general formula

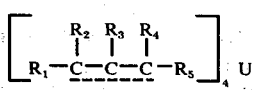

wherein $R_1$, $R_2$, $R_3$, $R_4$ and $R_5$, which may be the same or different, may be hydrogen atoms, alkyl radicals containing from 1 to 10 carbon atoms, aryl radicals containing from 4 to 10 carbon atoms and alkylaryl radicals, and the dotted line linking the three carbon atoms indicates the possible delocalization of the valence electrons of the double bond.

We have found, which is a subject of the invention, a process for the synthesis of novel uranium allyl compounds, which constitute the second subject of the invention and may be exemplified by the general formula

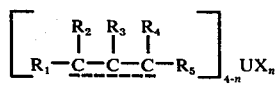

wherein the R groups have the aforesaid meaning, X is an anion such as $Cl^-$ $Br^-$ $I^-$ and $n$ is an integer ranging from 1 to 3.

The compounds constituting the subject of the invention can be prepared according the following general reactions

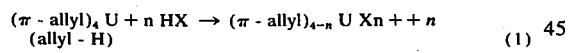

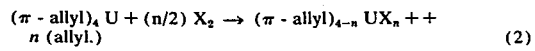

in which HX and $H_2$ respectively mean halide acids and halogens such as HCl, HBr, HI, $Cl_2$, $Br_2$, and $I_2$.

The foregoing reactions are carried out by dissolving the starting uranium tetra-$\pi$-allyl in an aliphatic, aromatic or cyclic ether solvent, e.g., diethylether, dibutylether, diphenylether, tetrahydrofuran, tetrahydropyran, and so on, and by adding the calculated amount, according to the preceding reactions (1) or (2), of XH or $X_2$ dissolved in the same solvent.

The reaction temperature is kept in the range from −78° to +50° C. The product is recovered by filtration and washed in filter by solvent still at low temperature.

All the isolated compounds are unstable in air and moisture and have to be treated and maintained an inert gas atmosphere.

The respective compounds obtained as aforesaid can be advantageously employed as catalyst in the polymerization or oligomerization of unsaturated compounds and particularly in the stereospecific polymerization of diolefins as described in a copending application of the same applicant.

EXAMPLE 1

20 mmoles of tetra ($\pi$-allyl) U (8g) were dissolved in 100 cm$^3$ of diethyl ether at −40° C and, under stirring, 20 mmoles of H Cl dissolved in 150 cm$^3$ of same solvent were slowly added.

The addition was carried out in about 4 hours at −40° C. At the end of the addition the suspension was filtered on a porous septum constituted by of sintered glass, cooled at same temperature, and the recovered precipitate was washed on the filter with three portions of ether, each of them consisting of about 20 cm$^3$, previously cooled.

The precipitate was dried under high vacuum, again at the temperature of −40° C and a dark violet crystalline solid was obtained. The yield was 85% calculated on uranium.

| Analysis: Calculated for $(C_3H_5)_3UCl$ | U 60% |
|---|---|
| | C 27.20% |
| | H 3.88% |
| | Cl 8.92% |
| | U 58.90% |
| | C 27.50% |
| | H 4.01% |
| | Cl 8.85% |

EXAMPLE 2

By working according to the procedure referred to in the foregoing example, 6.03 g (15 mmoles) of tetra ($\pi$-allyl) U in 100 cm$^3$ of ethyl ether were reacted with 15 mmoles of H I dissolved in 150 cm$^3$ of ether at the temperature of −35° C. After filtration and drying a black-violet solid was obtained at a yield of 90%.

| Theoretical for $(C_3H_5)_3UI$ | U | 48.74% |
|---|---|---|
| | C | 22.20% |
| | H | 3.05% |
| | I | 26.01% |
| | U | 47.50% |
| | C | 24.00% |
| | H | 3.20% |
| | I | 25.60% |

EXAMPLE 3

The compound of example 2 may be synthetized starting from U $(C_3H_5)_4$ and $I_2$ instead of H I. According to the foregoing procedure 17 mmoles (6.8 g) of tetra-allyl uranium were reacted with the stoichiometric amount of $I_2$ in ethyl ether.

After filtration, washing and drying a solid was isolated which was analyzed as follows:

| Found | U 47.30% |
|---|---|
| | I 25.30% |

EXAMPLE 4

($\pi$- $C_3H_5)_2$ U $Cl_2$ was synthesized. In this case the reaction was carried out in tetra-hydrofuran in order to avoid the insolubility of the intermediate constituted by the mono-halogen derivative. 9.5 mmoles of tetra-allyl uranium, dissolved in 100 cc of THF, were reacted, at −60° C, with 19 mmoles of H Cl dissolved in 30 cc of the same solvent.

At the end, 50 cm³ of ethyl ether, cooled to facilitate the total precipitation of the product, were added to the reaction mixture.

It was filtered, washed before with ethyl ether and then with cold pentane, and was dried at −30° C under high vacuum.

The yield was 6.5 mmoles of ($\pi$ - $C_3H_5$)$_2$ U $Cl_2$ crystallizing with 2 molecules of THF.

| Calculated for ($C_3H_5$)$_2$$UCl_2$ . 2 $C_4H_8O$ | U | 44.6% |
|---|---|---|
| | C | 31.50% |
| | H | 4.87% |
| | Cl | 13.30% |
| | U | 43.30% |
| | C | 29.80% |
| | H | 4.30% |
| | Cl | 13.4% |

What we claim is:
1. Uranium allyl compounds having the general formula

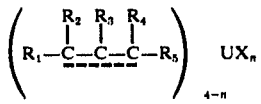

in which $R_1$, $R_2$, $R_3$, $R_4$, and $R_5$ are the same or different and are selected from the group consisting of hydrogen atoms, alkyl radicals having from 1 to 10 carbon atoms, aryl radicals having from 6 to 10 carbon atoms, cycloalkyl radicals having from 4 to 10 carbon atoms, and alkyl aryl radicals having from 7 to 10 carbon atoms, and the dotted line linking the three carbon atoms indicates the possible delocalization of the valence electrons; X is an anion selected from the group consisting of Cl⁻, Br⁻, and I⁻, and $n$ is an integer ranging from 1 to 3.

* * * * *